(12) United States Patent
Franco Rodriguez et al.

(10) Patent No.: US 11,918,682 B2
(45) Date of Patent: *Mar. 5, 2024

(54) INJECTABLE COMPOSITION WITH AROMATASE INHIBITOR

(71) Applicant: Laboratorios Farmacéuticos ROVI, S.A., Madrid (ES)

(72) Inventors: Guillermo Franco Rodriguez, Madrid (ES); Ibon Gutierro Aduriz, Granada (ES)

(73) Assignee: Laboratorios Farmacéuticos ROVI, S.A., Madrid (ES)

( * ) Notice: Subject to any disclaimer, the term of this patent is extended or adjusted under 35 U.S.C. 154(b) by 321 days.

This patent is subject to a terminal disclaimer.

(21) Appl. No.: 17/172,771

(22) Filed: Feb. 10, 2021

(65) Prior Publication Data

US 2021/0169778 A1    Jun. 10, 2021

Related U.S. Application Data

(60) Continuation of application No. 16/294,052, filed on Mar. 6, 2019, now Pat. No. 10,933,015, which is a division of application No. 14/610,362, filed on Jan. 30, 2015, now Pat. No. 10,285,936, which is a continuation-in-part of application No. PCT/EP2013/065877, filed on Jul. 29, 2013, and a continuation-in-part of application No. 14/555,273, filed on Nov. 26, 2014, now Pat. No. 10,350,159, which is a continuation-in-part of application No. PCT/EP2013/061319, filed on May 31, 2013, said application No. 14/610,362 is a continuation-in-part of application No. 14/555,287, filed on Nov. 26, 2014, now Pat. No. 10,335,366, which is a continuation-in-part of application No. PCT/EP2013/061320, filed on May 31, 2013, said application No. 14/610,362 is a continuation-in-part of application No. 13/690,647, filed on Nov. 30, 2012, now Pat. No. 10,085,936, which is a continuation-in-part of application No. PCT/EP2011/059000, filed on May 31, 2011, said application No. 14/610,362 is a continuation-in-part of application No. 13/690,707, filed on Nov. 30, 2012, now Pat. No. 10,058,504, which is a continuation-in-part of application No. PCT/EP2011/059001, filed on May 31, 2011.

(30) Foreign Application Priority Data

| May 31, 2010 | (EP) | 10382153 |
| May 31, 2011 | (EP) | 10382154 |
| May 31, 2012 | (EP) | 12170362 |
| May 31, 2012 | (EP) | 12170366 |
| Aug. 2, 2012 | (ES) | P201231271 |

(51) Int. Cl.
| A61K 9/00 | (2006.01) |
| A61K 31/4196 | (2006.01) |
| A61K 47/34 | (2017.01) |

(52) U.S. Cl.
CPC ........ *A61K 9/0024* (2013.01); *A61K 31/4196* (2013.01); *A61K 47/34* (2013.01)

(58) Field of Classification Search
None
See application file for complete search history.

(56) References Cited

U.S. PATENT DOCUMENTS

| 3,636,956 | A | 1/1972 | Schneider |
| 3,773,919 | A | 11/1973 | Boswell |
| 4,389,330 | A | 6/1983 | Tice |
| 4,523,591 | A | 6/1985 | Kaplan |
| 4,530,840 | A | 7/1985 | Tice |
| 4,938,763 | A | 7/1990 | Dunn |
| 5,620,700 | A | 4/1997 | Bergren |
| 5,688,801 | A | 11/1997 | Mesens |
| 5,770,231 | A | 6/1998 | Mesens |
| 6,143,314 | A | 11/2000 | Chandrashekar |
| 6,331,311 | B1 | 12/2001 | Brodbeck |
| 6,528,080 | B2 | 3/2003 | Dunn |
| 6,565,874 | B1 | 5/2003 | Dunn |
| 6,630,155 | B1 | 10/2003 | Chandrashekar |
| 6,673,767 | B1 | 1/2004 | Brodbeck |
| 6,773,714 | B2 | 8/2004 | Dunn |
| 6,803,055 | B2 | 10/2004 | Mesens |

(Continued)

FOREIGN PATENT DOCUMENTS

| EP | 2394663 A1 | 12/2011 |
| WO | WO 99/036071 A1 | 7/1999 |

(Continued)

OTHER PUBLICATIONS

Buzdar et al. Cancer vol. 95, No. 9, pp. 2006-2016. (Year: 2002).*
Wang et al. ("Design of a long-term antipsychotic in situ forming implant and its release control method and mechanism", Int. J. Pharm., May 10, 2012;427(2):284-92).
LIDE (Properties of Common Laboratory Solvents, CRC Handbook of Chemistry and Physics 84th Ed., 2003-2004, Sect. 15-14, CRC Press, New York).

(Continued)

*Primary Examiner* — Katherine Peebles
(74) *Attorney, Agent, or Firm* — INNOVAR, L.L.C.; Rick Matos

(57) ABSTRACT

The present invention provides a composition suitable for forming an intramuscular implant. It comprises a biodegradable thermoplastic polymer of polylactic acid (PLA), DMSO and an aromatase inhibitor compound. The invention also provides a kit suitable for the in situ formation of the composition and its use as a medicine for treating cancer, especially breast cancer.

22 Claims, 3 Drawing Sheets

(56) References Cited

U.S. PATENT DOCUMENTS

| | | |
|---|---|---|
| 7,118,763 B2 | 10/2006 | Mesens |
| 8,076,448 B2 | 12/2011 | Moore |
| 8,221,778 B2 | 7/2012 | Siegel |
| 8,324,343 B2 | 12/2012 | Moore |
| 10,058,504 B2 | 8/2018 | Gutierro Aduriz et al. |
| 10,085,936 B2 | 10/2018 | Gutierro Aduriz et al. |
| 10,182,982 B2 | 1/2019 | Gutierro Aduriz et al. |
| 10,195,138 B2 | 2/2019 | Gutierro Aduriz et al. |
| 10,285,936 B2 | 5/2019 | Franco Rodríguez et al. |
| 10,335,366 B2 | 7/2019 | Gutierro Aduriz et al. |
| 10,350,159 B2 | 7/2019 | Gutierro Aduriz et al. |
| 10,912,735 B2 * | 2/2021 | Franco Rodriguez .................. A61K 9/0024 |
| 10,933,015 B2 * | 3/2021 | Franco Rodriguez .................. A61K 31/4196 |
| 2002/0009492 A1 | 1/2002 | Truong |
| 2002/0023409 A1 | 2/2002 | Py |
| 2003/0165571 A1 | 9/2003 | Alkermes |
| 2004/0010224 A1 | 1/2004 | Bodmeier |
| 2004/0247870 A1 | 12/2004 | Brown |
| 2005/0042294 A1 | 2/2005 | Thanoo |
| 2006/0121085 A1 | 6/2006 | Warren |
| 2006/0210604 A1 | 9/2006 | Dadey |
| 2007/0003596 A1 | 1/2007 | Tittelbach |
| 2007/0077304 A1 | 4/2007 | Luk |
| 2007/0275068 A1 | 11/2007 | Martens |
| 2008/0206303 A1 | 8/2008 | Gellert |
| 2008/0287464 A1 | 11/2008 | Wright |
| 2009/0264491 A1 | 10/2009 | Mckay |
| 2009/0305957 A1 | 12/2009 | Moore |
| 2010/0015195 A1 | 1/2010 | Jain |
| 2010/0021544 A1 | 1/2010 | Bourges |
| 2010/0266655 A1 | 10/2010 | Dadey |
| 2010/0292195 A1 | 11/2010 | Dadey |
| 2012/0108511 A1 | 5/2012 | Moore |
| 2013/0177603 A1 * | 7/2013 | Gutierro Aduriz .. A61K 9/0002 514/383 |
| 2015/0147398 A1 | 5/2015 | Gutierro Aduriz et al. |
| 2015/0150791 A1 | 6/2015 | Gutierro Aduriz et al. |
| 2019/0117554 A1 | 4/2019 | Gutierro Aduriz et al. |
| 2019/0151230 A1 | 5/2019 | Gutierro Aduriz et al. |

FOREIGN PATENT DOCUMENTS

| | | |
|---|---|---|
| WO | WO 02/038185 A2 | 5/2002 |
| WO | WO 2007/041410 | 4/2007 |
| WO | WO 2008/059058 | 5/2008 |
| WO | WO 2008/153611 | 12/2008 |
| WO | WO2009/060473 | 5/2009 |
| WO | WO 2009/060473 A1 | 5/2009 |
| WO | WO 2011/151355 A1 | 12/2011 |
| WO | WO 2011/151356 A1 | 12/2011 |
| WO | WO 2013/178811 A1 | 12/2013 |
| WO | WO 2013/178812 A1 | 12/2013 |
| WO | WO 2014/019972 A1 | 2/2014 |

OTHER PUBLICATIONS

Gouw et al. (Physical Properties of Triglycerides IV. Dielectric Constant, Fette Seifen Anstrichmittel, (1967), 69(4), 223-226).

* cited by examiner

INJECTABLE COMPOSITION WITH AROMATASE INHIBITOR

CROSS-REFERENCE TO EARLIER FILED APPLICATIONS

The present application claims the benefit of and is a continuation of Ser. No. 16/294,052, filed Mar. 6, 2019, which is a division of Ser. No. 14/610,362 filed Jan. 30, 2015, which is a continuation-in-part of PCT/EP2013/065877, filed Jul. 29, 2013, which claims the benefit of ES P201231271 filed Aug. 2, 2012, and said application Ser. No. 14/610,362 is also a continuation-in-part of and claims the benefit of Ser. No. 14/555,273, filed Nov. 26, 2014, now U.S. Ser. No. 10/350,159 issued Jul. 16, 2019, which is a continuation-in-part of PCT/EP2013/061319, filed May 31, 2013, which claims the benefit of EP 12170366.4, filed May 31, 2012, and said application Ser. No. 14/610,362 is also a continuation-in-part of and claims the benefit of Ser. No. 14/555,287, filed Nov. 26, 2014, now U.S. Ser. No. 10/335,366 issued Jul. 2, 2019, which is a continuation-in-part of and claims the benefit of PCT/EP2013/061320, filed May 31, 2013, which claims the benefit of EP 12170362.3, filed May 31, 2012, and said application Ser. No. 14/610,362 is also a continuation-in-part of Ser. No. 13/690,647 filed Nov. 30, 2012, now U.S. Pat. No. 10,085,936 issued Oct. 2, 2018, which is a continuation-in-part of PCT/EP2011/059000, filed May 31, 2011, which claims the benefit of EP 10382154.2 filed May 31, 2010, and said application Ser. No. 14/610,362 is also a continuation-in-part of Ser. No. 13/690,707, filed Nov. 30, 2012, now U.S. Pat. No. 10,058,504 issued Aug. 28, 2018, which is a continuation-in-part of PCT/EP2011/059001, filed May 31, 2011, which claims the benefit of EP 10382153.4 filed May 31, 2010, the entire disclosure of each of the above-cited patents and applications being hereby incorporated herein by reference.

FIELD OF THE INVENTION

The present patent application is directed toward compositions useful in cancer therapies.

In particular, the present invention refers to a composition suitable for forming an intramuscular implant comprising a biodegradable thermoplastic polymer of polylactic acid (PLA), dimethyl sulphoxide (DMSO) and an aromatase inhibitor compound, a suitable kit for the in situ preparation of the composition and its use as a medicine for the treatment of breast cancer.

BACKGROUND OF THE INVENTION

Without doubt, cancer treatments need to be developed, not only new molecular entities but also pharmacological products for improving patients' quality of life. In this sense, the development of prolonged release formulations signifies an advance because they enable reducing the total dose administered, increasing the duration of each dose and the number of administrations and thereby creates a positive impact on the emotional state of the patient.

The active ingredients (drugs) letrozole and anastrozole are the first line active ingredients in the adjuvant treatment of postmenopausal women with hormone receptor-positive advanced breast cancer for whom there is no alternative therapy beyond daily administration of a tablet.

Letrozole (4,4'-(1,2,4-triazol-1-ylmethyl)dibenzonitrile) and anastrozole (2,2'-[5-(1H-1,2,4-triazol-1-ylmethyl)-1,3-phenylene]bis(2-methylpropanenitrile)) belong to a class of drugs called non-steroidal inhibitors of aromatase and their mechanism of action consists of reducing the amount of oestrogen in the body. This effect can decelerate or stop the growth of many types of cancer-producing cells in the breast that need oestrogen to grow.

Currently, there is no formulation of letrozole on the market with the ability to control the release of the drug over a long period of time. The pharmaceutical drug letrozole is currently only available in tablet form for daily oral administration. The formulations of letrozole described here enable obtaining therapeutic levels of the drug in blood from the start and continuously over a period of three months, avoiding the need for daily dosing regimes and thereby improving the patient's quality of life.

In the treatment of breast cancer, as in the treatment of cancer in general, the psychological state of the patient is very important; therefore the development of a three-monthly formulation of letrozole and/or anastrozole means a substantial improvement in their quality of life, reducing the impact that would result from daily treatment. In turn, medical examinations that are carried out during monitoring of the disease are normally conducted at 3 and 6 months over the first few years, so the administration of the formulation could coincide with consultancy visits to the doctor.

Similar reasoning has led to the appearance on the market of formulations such as Zoladex®, a preformed implant of goserelin for subcutaneous three-monthly application for the treatment of prostate carcinoma, and Implanon®, a preformed implant of etonogestrel used as a contraceptive. However, these preformed implants show a series of disadvantages including:

The preparation of the implants by extrusion requires the use of high temperatures, which can cause the degradation of the active ingredient and the generation of potentially toxic impurities;

Low homogeneity of the product obtained when including active ingredients at low doses;

Need for surgical procedures for implanting or injection of the implant using large diameter needles.

It is also possible to find in the literature some publications on implantable compositions of letrozole and/or anastrozole such as the following.

For example, WO 2008/041245 describes implantable compositions comprising a wide variety of active ingredients such as some aromatase inhibitors, including anastrozole, in a wide variety of administration forms from preformed microparticles suspended in an aqueous vehicle to formulations that gellify in situ. Although it is doubtful that this document can sufficiently support all the combinations of active ingredients and administration forms that may arise, the examples always refer to preformed microparticles, that is it never describes systems of forming implants directly "in situ". Finally, it should be pointed out that none of the examples show a duration of over 60 days.

WO 2010/065358 A1 describes compositions for the administration of medicines containing testosterone and an aromatase inhibitor for continuous administration of testosterone and for preventing its conversion to estradiol. Although the description considers the possibility that the form of administration may be an implant, the only example of a form of administration is pellets.

WO 2012/074883 A1 describes biodegradable compositions for administration of pharmaceutical drugs. These compositions require the use of water-insoluble solvents such as benzyl benzoate or benzyl alcohol in order to maintain the implant in a liquid or semi-solid state. These solvents have been previously shown to provide sudden releases and therefore are not suitable for the prolonged release compositions of the present invention.

US 2008/0206303 A1 describes prolonged release formulations of anastrozole comprising a PLA or PLGA polymer that can be accompanied by a wide variety of solvents; however, in the embodiments of the invention, the solvents used are benzyl alcohol and n-methyl-2-pyrrolidone (NMP), solvents that give rise to a very large burst followed by a subsequent almost zero release. In fact, the burst that was acceptable for the inventors in this document was 25-30% in one day, a very high value, and because of this none of their examples lasted more than 60 days; in particular in dogs, animals similar to humans, release did not continue longer than 35 days. Finally, no mention was made in this document of letrozole particle size nor of the importance of this factor in the behavior of the formulation.

Therefore, it would be desirable to obtain a three-monthly formulation of letrozole and/or anastrozole for first line adjuvant treatment of breast cancer in hormone receptor-positive postmenopausal women.

SUMMARY OF THE INVENTION

For this reason, the implants of the invention that are formed in situ overcomes the majority of the drawbacks presented by current formulations based on preformed implants. It offers an alternative practical and effective therapy for the patient achieving therapeutic profiles lasting for at least 60 days.

The term initial "burst" is understood as the ratio of the area under the curve of plasma levels of the active ingredient (drug) in living animals obtained over the first 72 hours after intramuscular administration of the product relative to the total area under the curve (also termed "AUC") obtained at the end of a specified period, e.g. 30 days, 60 days or 90 days, after the injection of an amount of letrozole or anastrozole.

In order to obtain a prolonged release of active ingredient suitable for the object of the present invention, the area under the curve of the burst is less than 10% compared to the total AUC, and ideally less than 5%. Similarly, obtaining an equilibrium in the or a more level prolonged release profile of the aromatase inhibitor over at least 60 days requires that no more than 50% of the area under the curve of plasma levels is obtained over the first 30 days after the injection. In other words, the preferred prolonged release of active ingredient is such that the area under the curve of the burst is less than 10% of the total AUC and not more than 50% of the total AUC is obtained over the first 30 days after injection.

In some embodiments, the injectable depot composition provides a plasma level profile for drug as follows.

A first aspect of the invention provides a composition suitable for forming an intramuscular implant comprising a biodegradable thermoplastic polymer of polylactic acid (PLA), DMSO and an aromatase inhibitor compound of general formula (1):

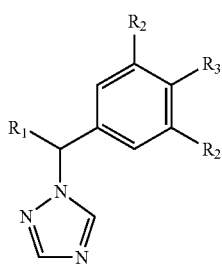

(1)

wherein:
When $R_1$ is H $R_2$ is

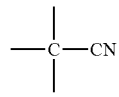

and $R_3$ is H
When $R_1$ is

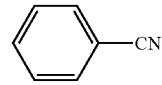

$R_2$ is H and $R_3$ is CN characterized in that: a) the aromatase inhibitor compound is in suspension in a solution containing DMSO and PLA and represents between 15-50% by weight of the total composition; b) the composition being able to solidify, to form a solid or gel-type implant on contact with an aqueous fluid or with the fluid of the body; and c) the composition providing therapeutic plasma concentrations, after in vivo administration, of at least 100 nmol/mL for not less than, for at least or for more than 60 days following administration. The plasma levels of letrozole should be sufficient to provide an in vivo suppression of serum estrogens (E1 and E2) of at least about 50% (E2, estradiol) and 70% (E1, estrone) and preferably of at least about 60% (E1) and 80% (E2) in the steady state during a dosing period. Some individual subjects may, on an equivalent dose basis, exhibit plasma concentrations outside the ranges specified herein for reasons such as poor health, advanced age, compromised metabolism, renal failure, disease, etc.

As used herein and unless otherwise specified, the drug or active ingredient included in the injectable composition can be present in free base, salt, amorphous, crystalline, anhydrous, hydrate, optically pure, optically enriched or racemic forms thereof. Combinations of these various forms are also within the scope of the invention. A prodrug, metabolite or derivative of the drug can also be included. In some embodiments, the drug is present in free base form.

In some embodiments, the aromatase inhibitor compound is in suspension in a solution containing DMSO and PLA and the aromatase inhibitor represents between 20-30% by weight of the total composition.

In some embodiments, the aromatase inhibitor compound is in suspension in a solution containing DMSO and PLA and aromatase inhibitor comprises about 25% by weight of the total composition.

According to another aspect, the aromatase inhibitor compound of general formula (1) has the following particle size distribution:
  <10% of the particles less than 20 microns,
  <10% of the particles greater than 350 microns and
  d0.5 between 70-200 microns.

In some embodiments, the aromatase inhibitor compound is letrozole or anastrozole, either alone or in combination. The ratio of letrozole to anastrozole in the composition can range from 100:0 to 0:100, respectively.

In some embodiments, the solution formed by DMSO and PLA comprises 40-43% by weight of PLA (100% lactic) and 57-60% by weight of DMSO.

In a further preferred embodiment, the terminal group of the PLA is as an ester instead of a carboxylic acid. In other words, the PLA is end-capped to form an ester moiety.

In some embodiments, the active ingredient is subjected to sterilization, for example by gamma or beta radiation. Sterilization by radiation of the active ingredient may be carried out prior to its inclusion in the implantable composition. The dose of radiation can be up to a maximum value of 35 kGy. Sterilization of the active ingredient can also be carried out by terminal radiation of the product.

In another embodiment, the weight ratio of DMSO to drug is in the range of about 0.5 to about 3.7, about 1:1 to about 3:1, about 1.5:1 to about 2:1 or about 1.7:1 to about 1.8:1.

In another embodiment, the viscosity of the solution containing DMSO and PLA is in the range of about 0.8 to about 1.8 Pa·s, about 0.8 to about 1.5 Pa·s, about 0.8 to about 1.3 Pa·s or about 1 to 1.2 Pa·s.

Another aspect of the invention concerns use of the injectable composition herein as a medicine for the treatment of breast cancer, meaning a method of treating cancer by administration of the injectable composition. The invention provides a method of treating a disease, condition or disorder that is therapeutically responsive to aromatase inhibitor comprising administering an amount (or volume) of injectable composition comprising a therapeutically effective amount of the aromatase inhibitor. The composition can be administered every 30, 45, 60 or 90 days.

In another embodiment, the maximum volume administered to a subject by intramuscular injection is about 2 mL and comprises a maximum of 500 mg of letrozole.

According to another aspect, the composition suitable for forming an intramuscular implant is characterized in that the AUC of the burst of the compound with the general formula (1) is not more than or is less than 10% of the total AUC and is not more than or is less than 50% of the total AUC over the first 30 days after injection.

A ready-to-use formulation can be prepared, for example, and included in a syringe ready for use for intramuscular injection. The same formulation may form part, for example, of a kit of two syringes, one male and one female or two male syringes linked by a connector in which the solution of polymer in DMSO is in one syringe and the aromatase inhibitor is in solid form in a second syringe.

Similarly, the final composition can be obtained by, for example, maintaining one syringe with the polymer and aromatase inhibitor in solid state and the solvent (DMSO) in a second syringe.

Reconstitution in these cases can be via direct joining of male and female syringes or by a connector where there are two male syringes, and pushing-pulling the plungers in both directions giving rise to the combination of the products, and in this way to the solution of the polymer and the suspension of the active ingredient.

Any alternative to this system that gives rise to the composition of the present invention is possible, so that any variation with other designs of the formulation, where the final combination results in the desired product, for example maintaining the solvent or polymer solution in a vial apart from the active ingredient, or for example keeping the polymeric solution in a preloaded syringe and the aromatase inhibitor in a vial so that the polymeric solution is injected into the vial to give rise to the formation of the suspension, will be considered as possible alternatives for the object of the present invention.

According to another aspect, the present invention provides a kit suitable for the in situ preparation of the composition of the present invention, wherein the aromatase inhibitor compound of general formula (1) and the polymer are in a first container in solid form and the DMSO is in a second separate container.

According to another aspect, the present invention refers to a kit suitable for the in situ preparation of the composition wherein the polymer has been lyophilized.

According to another aspect, the present invention refers to a suitable kit for the in situ preparation of the composition wherein the aromatase inhibitor compound of general formula (1) is in a first container in solid form and the DMSO and the polymer are in a second container in solution.

According to another aspect, the present invention refers to a suitable kit for the in situ preparation of the composition wherein the aromatase inhibitor compound of general formula (1), the polymer and the DMSO are in a single container in the form of a suspension.

BRIEF DESCRIPTION OF THE FIGURES

The following figures are provided to help with the interpretation of the object of the present invention, but do not imply any limitation.

DETAILED DESCRIPTION OF THE INVENTION

Figure 1:
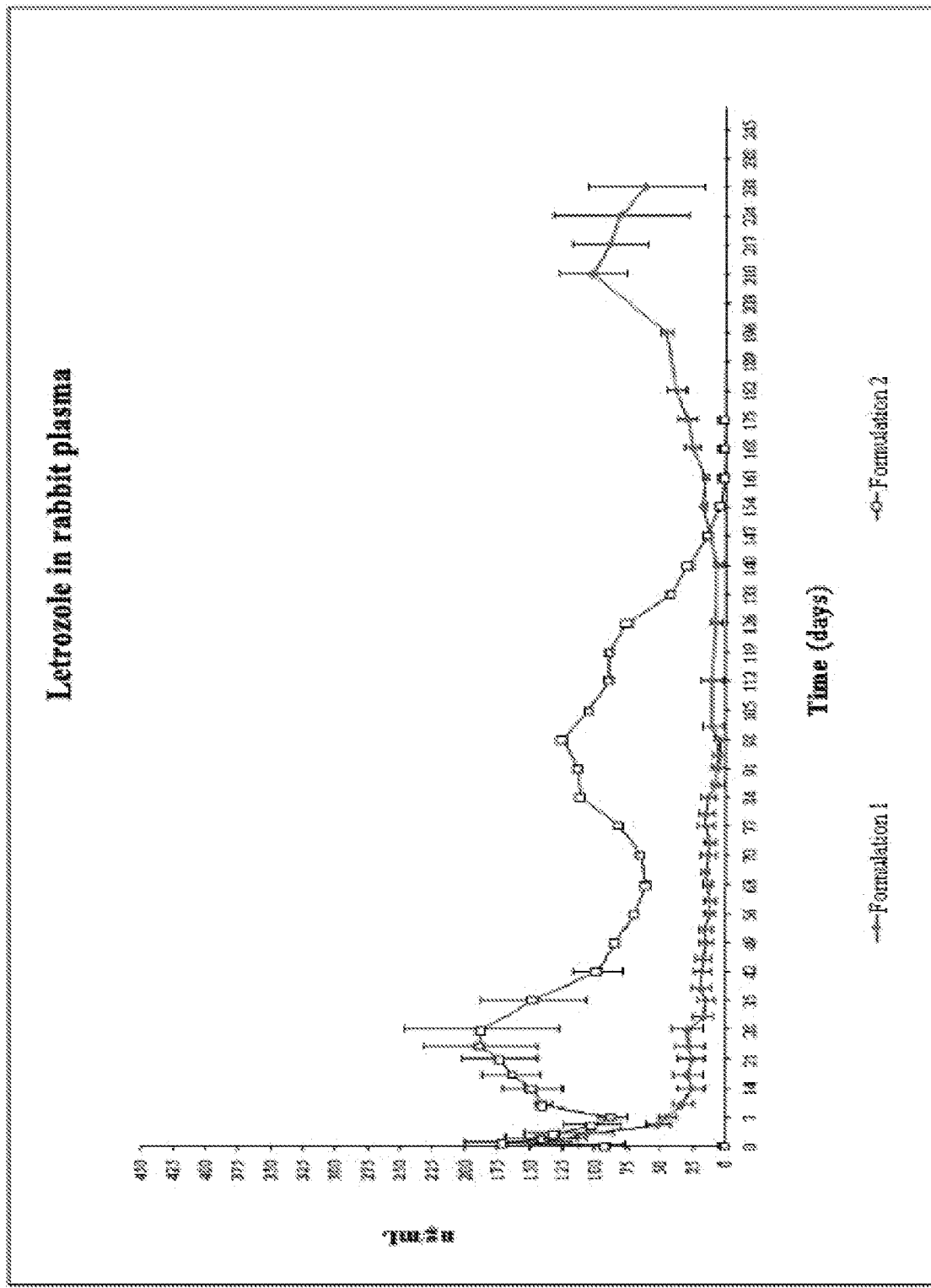
FIG. 1 depicts the plasma levels of letrozole (in ng/mL) obtained after intramuscular administration to New Zealand white rabbits of the formulations described in example 1. The values shown correspond to the mean plasma levels obtained in three animals of each group.

The following terms are used interchangeably unless otherwise specified: "PLA"; "biodegradable thermoplastic polymer of polylactic acid"; "lactic polyacid" and "polylactic acid"; "DMSO" and "dimethyl sulfoxide".

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. If not otherwise specified, the viscosity value of the polymeric solution or the injectable composition is given in Pa·s units.

Throughout the development of the present invention, the behavior of various parameters that might have an influence on the result of the implantable compositions for prolonged release in accordance with the invention have been investigated. The parameters were the following.

1. Rheological Properties of the Polymeric Solutions and Inherent Viscosity

The behavior of the fluid, both of polymer solutions and the complete formulation, was evaluated by rheometry. In the case of matrices being considered as a vehicle for letrozole, these all exhibited Newtonian behavior. Viscosity is used herein as an indirect parameter, related to the concentration of the polymer, for describing the behavior of the injectable formulation with respect to its ability to control the initial release of product.

The PLA polymer exhibits an inherent or intrinsic viscosity in the range of about 0.16-0.60 dl/g, or about 0.20-0.50 dl/g as measured in chloroform at 25° C. at a concentration of 0.1% wt/v with a Ubbelhode size 0c glass capillary viscometer or as measured in chloroform at 30° C. and at a concentration of 0.5% wt/v with a size 25 Cannon-Fenske glass capillary viscometer. The PLA polymer is selected from free acid (not end-capped) or end-capped (e.g. alkyl esters such as lauryl ester, methyl ester, etc., referred to herein as PLA-e) terminal carboxylic poly-lactide with polymer. The PLA polymer can be a poly(L-lactic acid) polymer, poly(D,L-lactic acid) polymer, poly (D-lactic acid) or a copolymer of those polymers. Polymers that are end-capped with esters (as opposed to the free carboxylic acid) demonstrate longer degradation half-lives. Suitable grades of PLA are commercially available from Uhde Inventa-Fischer (Berlin, DE), NatureWorks LLC (Blair, NE, USA), Plastic Ingenuity (Cross Plains, WI, USA), Toyobo, Dai Nippon Printing Co., Mitsui Chemicals, Shimadzu, NEC, Toyota (Japan), PURAC Biomaterials, Hycail (The Netherlands), Galactic (Belgium), Cereplast (U.S.A.), FkuR, Biomer, Stanelco, Inventa-Fischer (Germany), Snamprogetti (China), Boehringer Ingelheim (RESOMER® grades; Ingelheim Am Rhein, DE), Evonik Industries (RESOMER® grades; Essen, DE), ALKERMES (Dublin, Ireland) or SIGMA ALDRICH (ST. Louis, MO). In some embodiments, the PLA is end-capped with an alkyl alcohol to form an ester end group moiety. The uncapped PLA typically provides a faster initial release of drug in the first 30 days of a dosing period than does the PLA-e (see example below).

It was determined that the polymer solution should have a minimum viscosity of about 0.8 Pa·s, although this may preferably be around 1 Pa·s, but not greater than about 1.8 Pa·s. The viscosity of the polymer solution can range from about 0.7 to about 2 Pa·s, about 0.8 to about 1.8 Pa·s or about 1 to about 1.8 Pa·s. Polymer solutions, in DMSO and measured at 25° C., which are obtained within this viscosity range, provide the appropriate balance between solubilization of the active ingredient and its retention in the polymeric matrix, thereby providing clinically relevant plasma concentrations of letrozole or anastrozole, avoiding or minimizing release of excessive amounts of the active ingredient that may compromise the useful life of the implant during the diffusion phase of the active ingredient. When the active ingredient is added, the viscosity increases, but the viscosity preferably does not exceed 4 or 3 Pa·s.

The following tables show the apparent viscosity of the most suitable polymers in vitro and in vivo at different concentrations in DMSO at 25° C., as well as the viscosity of a final preferred formulation.

Viscosity of the PLA polymer Resomer® R 203 S, irradiated as raw material by beta radiation at a dose of 10 kGy,

|  | D,L-lactic polymer (% by w) | | | |
| --- | --- | --- | --- | --- |
| Viscosity (Pa · s) | 40% | 41.5% | 43% | 45% |
| mean | 0.874 | 1.020 | 1.295 | 1.645 |
| SD | 0.043 | 0.021 | 0.038 | 0.016 |

Viscosity of a Preferred Formulation

| Viscosity (Pa · s) | | |
| --- | --- | --- |
| Replicated | mean | SD |
| 2.462 | 2.514 | 0.045 |
| 2.536 | | |
| 2.543 | | |

2. Particle Size of the Active Ingredient

The particle size of the active ingredient has an effect upon the final behavior of the formulation as it directly affects the process of release from the formulation once it has been administered. The importance of this fundamental fact has not been previously described in documents describing the preparation of prolonged release formulations containing aromatase inhibitors.

The use of different size fractions was evaluated in order to determine or narrow an interval that is suitable and as well defined as possible. Better than a specific and totally narrow size, it is more useful to have a distribution of various crystal sizes enabling, to a certain extent, modulation of release in a staggered way. In this way, the smallest sizes (below 50 microns) are not preferred because they very easily diffuse with the solvent during the formation of the implant. Particles of intermediate sizes, with mean values close to 100-300 microns, are useful because they are retained by the matrix, require more time to dissolve and remain trapped in the implant during its solidification. Particles above 300 microns require a high degree of degradation of the polymer, resulting in new latency periods in the life cycle of the implant and excessive releases at the time of hydrolysis of the polymer, so the use of a high percentage or particles in this size range is not preferred.

It has been determined that elimination or reduction in the amount not only of the smallest sizes but also of the intermediate to low sizes (50-100 microns) provides improvement to the product, given that, on the one hand, the final viscosity of the reconstituted product is reduced and, on the other hand, the pronounced burst effect is substantially prevented. Based upon the above, the active ingredient can possess a particle size distribution characterized as follows: not more than 10% of the total volume of drug particles are less than 20 microns in size (equivalent diameter in volume as a function of applying Fraunhofer theory to irregularly shape particles; as measured by laser light scattering, such as with a Malvern Mastersizer 2000) and not more than 10% of the total volume of drug particles are greater than 350 microns in size. In addition, the drug particles can possess a d0.5 value preferably in the range of about 70-200 microns.

In some embodiments, the drug exhibits one of the following particle size distributions:

| | Parameter | | | | | | | | |
|---|---|---|---|---|---|---|---|---|---|
| | I | II | III | IV | V | VI | VII | VIII | VIII |
| d0.1 (microns) | 38 | 40 | 29 | 31 | ≥20 | <70 | ≥20 | ≥20 | ≥20 |
| d0.5 (microns) | 141 | 152 | 103 | 125 | 70-200 | 70-200 | 70-200 | 70-125 | 125-200 |
| d0.9 (microns) | 312 | 320 | 245 | 304 | ≤350 | ≤350 | >200 | ≤350 | ≤350 |

If not otherwise specified, the particle size distribution was determined by light scattering technique using laser light diffraction in wet mode. It is known that particle size distribution results can be altered as a function of the material treatment such the use of high concentrate surfactant agents and/or strong force energies (vortex, sonication, etc). If nothing else is mentioned, drug is not treated and samples are prepared by direct addition to the tank under moderate stirring (2000-3500 rpm). The methodology applied on present invention to determine the drug particle size distribution mimics in a more faithfully way the behavior of the drug powder on the injectable formulation herein described than other methods which apply force energies to the sample and/or use high concentrate surfactant agents for preparing the samples in order to achieve high degrees of powder disaggregation that cannot be simulated during the manual reconstitution process of the formulation.

3. Degree of Suspension of the Active Ingredient in the Solution Containing the PLA and the DMSO.

The presence of the active ingredient in solution or in suspension affects the process of release of the active ingredient once the formulation is injected intramuscularly. When drug is completely dissolved in the solution containing the polymer and DMSO, the intramuscular injection of the formulation gives rise to the release of an excessive amount over the first few days due to the diffusion of letrozole together with water-miscible solvent during the hardening process of the polymeric carrier, followed by a latency period in which in vivo release of the active ingredient is minimal and the final release of drug occurs at the time when the polymer experiences degradation by hydrolysis. We describe herein how only formulations containing drug in suspension are capable of controlling the initial release of the active ingredient and of preventing these periods of latency in which the formulation is not clinically effective.

In some embodiments, the drug is partially dissolved or completely undissolved in the polymeric solution. In some embodiments, ≤5%, ≤10%, ≤20% wt of the drug is dissolved in the solvent or polymeric solution to form the injectable composition. In some embodiments, >0%, ≥0.5%, ≥1%, ≥5%, or ≥10% wt. of the drug is dissolved in the solvent or polymeric solution to form the injectable composition.

4. Weight Ratios and Content of Components

In some embodiments, the injectable composition comprises DMSO, drug and PLA. The composition can include one or more additional components that do not negatively impact the performance of the composition after administration to a subject. If present, such other component(s) can be present in a total amount of ≤20% wt, ≤15% wt., ≤10% wt, ≤5% wt, ≤1% wt. or ≤0.1% wt based upon the total weight of the composition. In some embodiments, the injectable composition consists essentially of or consists of DMSO, drug and PLA.

A characteristic of the present composition is that the aromatase inhibitor compound of general formula (1) is suspended, and preferably present in an amount close to 25% by weight of the total composition, in a solution containing DMSO and PLA, which in some embodiments make up the remaining 75% by weight of the total composition. As detailed in Example 1 if, for example, when the aromatase inhibitor compound is completely in solution, the in vivo response is unsatisfactory.

In some embodiments, the weight or mass ratio of DMSO to drug is in the range of about 0.5 to about 3.7, about 1:1 to about 3:1, about 1.5:1 to about 2:1 or about 1.7:1 to about 1.8:1.

In some embodiments, the weight or mass ratio of DMSO to PLA is about 1:1 to about 2.3:1, about 1.2:1 to about 1.8:1, about 1.3:1 to about 1.5:1, or about 1.4:1.

In some embodiments, the weight or mass ratio of polymer solution to drug is about 1:1 to about 5.7:1, about, 2.3:1 to 4:1, about 2.8:1 to about 3.2:1, or about 3:1.

In some embodiments, the weight or mass ratio of PLA to drug is about 0.6:1 to about 2.8:1, about 1.0 to 2.0, about 1.1:1 to 1.6:1, or about 1.2:1.

4. Method of Treatment

The invention provides a method of treating a disease, disorder or condition that is therapeutically responsive to aromatase inhibitor. Exemplary diseases, disorders or conditions include, for example: a) adjuvant treatment (treatment following surgery with or without radiation) of post-menopausal women with hormone receptor-positive early breast cancer; b) metastasis in both pre and post-menopausal women; c) precocious puberty or children with pubertal gynecomastia; d) reducing estrogens, including estradiol, in men; e) hormonally-responsive breast cancer after surgery; f) ovarian stimulation; g) promote spermatogenesis in male patients suffering from nonobstructive azoospermia; h) endometriosis; i) cancer that is estrogen hormone receptor-positive or sensitive (non-small cell lung cancer, uterine leiomyomas, etc.); j) infertility in women with polycystic ovarian syndrome; k) ovarian cancer; l) breast cancer that is estrogen hormone receptor positive or sensitive; j) priming for in vitro maturation cycles; k) preoperative treatment with letrozole in premenopausal women undergoing laparoscopic myomectomy of large uterine myomas; l) short stature in peripubertal boys; m) unexplained infertility or infertility with unknown or uncertain etiology; n) idiopathic central precocious puberty in boys.

The method comprises administering an amount (or volume) of injectable composition comprising a therapeutically effective amount of the aromatase inhibitor. The composition can be administered every 30, 45, 60, 90, 120 or 150 days, or every month, every two months, every three months, every four months, every five months, every six months, or as often as needed for as many times needed to ameliorate the disease, disorder or condition. Combinations of the dosing regimens herein are contemplated. The composition provides therapeutic plasma levels for a period of at least 1, at least 2, at least 3, at least 4, at least 5 or at least 6 months following administration of a dose of aromatase inhibitor.

A dose of letrozole administered at the beginning of a dosing period will typically range from about 50 to about 750 mg, and the dose is typically included in an approximate volume of injectable composition ranging from about 0.1 to about 3 ml.

A dose of anastrozole administered at the beginning of a dosing period will typically range from about 30 to about 200 mg, and the dose is typically included in a volume of injectable composition ranging from about 0.1 to about 1.5 ml.

The intramuscular dose can be administered to any muscle or muscle group typically recognized by the pharmaceutical industry as a suitable site for an injectable composition. In some embodiments, the composition is administered to the gluteal and/or deltoid muscles. The composition can also be administered to the quadriceps muscle group.

Administration of a single dose is typically considered that amount of injectable composition administered to a subject within a period of up to 24 hours, up to 12 hours, up to 6 hours, up to 3 hours, up to one hour, up to 30 min, up to 15 min or up to 5 min.

A dose of injectable composition refers to an amount of injectable composition comprising a specified dose of drug. For example, a dose of 25-200 mg of injectable composition comprises a dose of 25-200 mg of drug; therefore, the actual amount of injectable composition administered would be greater than 25-200 mg, the actual amount of injectable composition being determined according to the content drug in the injectable composition. The composition can also be used to administer drug according to other dosing regimens accepted by the regulatory and clinical communities. The dose can be administered on a mg of drug per kg of body weight basis.

A dose can be administered to a single muscular site or can be divided into two or more portions and administered to two or more muscular sites of a subject. For example, a first portion of a dose can be administered to a first section of gluteal muscle and a second portion of the dose can be administered to a second section of gluteal muscle of a subject.

As used herein, the term "dosing period" refers to the period of days or weeks as measured from the initial day after administration of a dose to at least 30 days, at least 45 days, at least 60 days, at least 90 days, at least 120 days, etc. after administration or to administration of a subsequent dose. During the dosing period, the implant will provide therapeutic plasma levels of drug for at least at least 1 month, at least two months, at least three months, at least four months, at least 5 months, or at least 6 months. A dosing period can end after expiration of a predetermined number of days or after the plasma level of drug drops below therapeutic levels.

As used herein, a "treatment period" refers to the weeks, months or years during which implants of the invention are administered to a subject. A treatment period generally comprises plural dosing periods. Dosing periods can occur sequentially or in an overlapping manner during a treatment period. For example, a first dose of injectable composition is administered and a second dose of injectable composition can be administered at a time following administration of the first dose, such that each dose will have its own corresponding dosing period, and the dosing periods would overlap. Dosing periods will typically be sequential or overlap by no more than one to seven days.

The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a single dosing period.

Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

In another embodiment, the injectable depot composition is sterile as a finished product. In another embodiment, the biocompatible polymer is sterilized previously to its aseptic filling process, preferably by irradiation or by other process, e.g. filtration.

The plasma concentration profile during the dosing period can exhibit one, two, or more maxima and one, two or more minima. An initial maximum can be caused by dissolution of drug during the initial day(s) of the dosing period followed by a slowing of the release thereof and another maximum can be caused by increased rate of release during the remaining days of the dosing period. Embodiments of the invention include those wherein: a) the plasma profile exhibits a maximum during the first third of the dosing period; b) the plasma profile exhibits a maximum during the second third of the dosing period; c) the plasma profile exhibits a maximum during the final third of the dosing period; and/or d) the plasma profile is substantially level (a standard deviation within ±30%, ±25%, ±20%, ±15%, ±10% or ±5% of the average or mean) during the dosing period.

The injectable depot composition provides an adequate plasma level profile for drug after administration during a dosing period. An "adequate plasma level profile" is considered as providing a burst of drug that is not more than or is less than 10% of the total AUC and is not more than or is less than 50% of the total AUC over the first 30 days after injection. In some embodiments, the area under the curve (AUC) of the burst is less than 10% compared to the total AUC, and ideally less than 5%, during a dosing period.

In some embodiments, the injectable depot composition provides a plasma level profile for drug as follows.

| Percentage of Drug total AUC During the Period Following Administration (day) | | |
|---|---|---|
| Day-0 up to day 3 | From day 3 to day 30 | From day 30 up to day 60 or end of dosing period |
| NMT 10% of total AUC | NMT 50% of total AUC | ≥50% of total AUC |
| NMT 5% of total AUC | NMT 50% of total AUC | ≥50% of total AUC |

The implant of the invention can provide substantially improved plasma levels of drug when compared to another injectable formulation (not according to the invention) containing the same drug when administered on an equivalent dose basis.

All values disclosed herein may have standard technical measure error (standard deviation) of ±10%. The term "about" is intended to mean ±10%, 5%, ±2.5% or ±1% relative to a specified value, i.e. "about" 20% means 20±2%, 20±1%, 20±0.5% or 20±0.25%.

EXAMPLES

The following examples are illustrative of the invention and are not to be considered limiting.

Example 1: Study of the Influence of the Physical Form of the Active Ingredient in the Formulation: Suspension Vs. Solution The influence of the physical form of letrozole in the injectable solution (solution vs. suspension of the active ingredient) was evaluated by the use of the formulation described below:

Formulation 1: Formulation with Letrozole in Solution

| | Ingredient | Amount (mg, % wt) |
|---|---|---|
| Syringe 2.25 ml male | Lactic acid polymer (ester terminal group) of intrinsic viscosity of 0.3 dl/g, irradiated as raw material at 10 kGy. | 55.20 (35.8%) |
| | Dimethyl sulfoxide | 82.80 (53.7%) |
| Syringe 2.25 ml female | Letrozole | 16.20 (10.5%) |

Weight ratio of DMSO to PLA is about 1.5:1. Weight ratio of polymer solution to letrozole is about 8.5:1. Weight ratio of PLA to letrozole is about 3.4:1. Weight ratio of DMSO to letrozole is about 5.1:1.

Formulation 2: Formulation with Letrozole in Suspension

| | Ingredient | Amount (mg) |
|---|---|---|
| Syringe 2.25 ml male | Lactic acid polymer (ester terminal group) of intrinsic viscosity of 0.3 dl/g, irradiated as raw material at 10 kGy. | 38.80 (30%) |
| | Dimethyl sulfoxide | 58.30 (45%) |
| Syringe 2.25 ml female | Letrozole | 32.40 (25%) |

Weight ratio of DMSO to PLA is about 1.5:1. Weight ratio of polymer solution to letrozole is about 3:1. Weight ratio of PLA to letrozole is about 1.2:1. Weight ratio of DMSO to letrozole is about 1.8:1.

Letrozole particle size in formulation 2 was characterized by the technique of laser ray diffraction (Malvern Mastersizer 2000, suspended in water until obscuration of 9.41%) and had the following distribution (in % volume): d(0.1)=38.21 µm, d(0.5)=141.35 µm and d(0.9)=312.13 µm.

In both cases, reconstitution of the product was carried out by connection of the male and female syringes and successive movements of the plungers in both directions until complete solution of the polymer had been achieved.

Study of In Vivo Release in New Zealand White Rabbits

Trials of in vivo release for the present document were carried out by determination of pharmacokinetic profiles of letrozole and anastrozole in plasma after intramuscular administration in experimental animal models, rabbits and/or dogs.

For quantification of letrozole in dog and rabbit plasma a technique based on high performance liquid chromatography with fluorescence detector HPLC-FLD with mass-mass detector using a liquid-liquid extraction with ethylene acetate as the organic solvent and resuspension for analysis in reverse phase with isocratic elution. Carvedilol was used as the internal standard and the process time was 8.5 min with a letrozole retention time of 7.8 min and applying wavelengths of 240 nm (λ excitation) and 315 nm (λ emission). The validated concentration interval was from 5 (LLOQ) to 500 ng/mL, that is with a lower limit of quantification or minimum quantifiable analyte concentration of the analytical technique of 5 ng/mL and a maximum validated concentration of 500 ng/mL. Calibration curves obtained were characterized with a correlation coefficient of over 0.99. Precision and intra-assay and inter-assay accuracy was less than 20% for the LLOQ and less than 15% for the other QCs, that is, of the other known concentration samples used as quality controls in conducting the analysis. The bioanalytical method was validated over three days and the results met the acceptance criteria described in the FDA guide: "Bioanalytical Method Validation".

Samples of letrozole in dog and rabbit plasma were demonstrated to be stable at room temperature for up to 6 hours. Processed samples could be stored in the sampler at 4° C. for 24 hours without noticing any change in the precision and accuracy of the analysis. Cycles of freezing/thawing carried out did not affect the stability of letrozole in dog and rabbit plasma. Long term stability of the samples stored at −80° C. demonstrated stability for 132 days.

Formulations 1 and 2 were administered intramuscularly in the gluteus muscle of New Zealand white rabbits with approximate body weight of 3 kg. Three animals were used for each group and they were injected with an amount of formulation corresponding to 5.4 mg/kg for formulation 1 and 10.8 mg/kg for formulation 2. After injection, samples of plasma were collected from the rabbits at previously established sampling times of up to 231 days after the injection. The results obtained are shown in FIG. 1. FIG. 1 shows that administration of the double dose of formulation 2 compared to formulation 1 in New Zealand white rabbits gave rise to similar initial plasma levels. Given that the dose used in formulation 1 was half that used in formulation 2, the clear importance of controlling the physical form of the active ingredient in the formulation could be seen. Letrozole, being in solution in formulation 1, diffuses with the solvent to a greater extent than in the case of letrozole in formulation 2. It can also be seen that in the case of formulation 1 the plasma levels fell swiftly, and did not start to recover until day 154 after injection, the time at which additional active ingredient is released due to the hydrolytic degradation of the polymer that retains it. Formulation 2 was able to maintain continuous significantly high levels of letrozole in rabbit plasma for more than 4 months.

Example 2: Study of the Influence of the Terminal Group of the Polymer

Evaluation of the influence of the terminal carboxylic or ester (N-capped) group of the polymer was evaluated by the use of the formulations described below:

Formulation 1: Formulation of Lactic Acid Polymer Terminating in a Carboxylic Group

| | Ingredient | Amount (mg) |
|---|---|---|
| Syringe 2.25 ml male | Lactic acid polymer (carboxylic terminal group) of intrinsic viscosity of 0.3 dl/g, irradiated as raw material at 10 kGy. | 38.80 |
| | Dimethyl sulfoxide | 58.30 |
| Syringe 2.25 ml female | Letrozole | 32.40 |

Weight ratio of DMSO to PLA is about 1.5:1. Weight ratio of polymer solution to letrozole is about 3:1. Weight ratio of PLA to letrozole is about 1.2:1. Weight ratio of DMSO to letrozole is about 1.8:1.

Formulation 2: Formulation with Lactic Acid Polymer Terminating in an Ester Group

| | Ingredient | Amount (mg) |
|---|---|---|
| Syringe 2.25 ml male | Lactic acid polymer (ester terminal group) of intrinsic viscosity of 0.3 dl/g, irradiated as raw material at 10 kGy. | 38.80 |
| | Dimethyl sulfoxide | 58.30 |
| Syringe 2.25 ml female | Letrozole | 32.40 |

Weight ratio of DMSO to PLA is about 1.5:1. Weight ratio of polymer solution to letrozole is about 3:1. Weight ratio of PLA to letrozole is about 1.2:1. Weight ratio of DMSO to letrozole is about 1.8:1.

Letrozole particle size in formulations 1 and 2 were characterized by the technique of laser ray diffraction (Malvern Mastersizer 2000, suspended in water until obscuration of 9.41%) and had the following distribution (in % volume): d(0.1)=38.21 µm, d(0.5)=141.35 µm and d(0.9)=312.13 µm.

In both cases, reconstitution of the product was carried out by connection of the male and female syringes and successive movements of the plungers in both directions until complete solution of the polymer had been achieved.

In parallel, the viscosity of the solution containing the components of the male syringe was evaluated, in amounts proportionally equivalent to those described (41.5% by weight of polymer with respect to the weight of solution) at 25° C. by the use of a rotational viscometer (Haake). The viscosity result values obtained are shown in the following table:

| Polymer (beta irradiated at 10 kGy as raw material) | Viscosity at 25° C. (Pa · s) |
|---|---|
| PLA-carboxylic terminal group | 1.221 |
| PLA-ester terminal group | 1.054 |

Study of In Vivo Release in New Zealand White Rabbits

In the present example, formulations 1 and 2 were administered intramuscularly in the gluteus muscle of New Zealand white rabbits with approximate body weight of 3 kg. Three animals were used for each group and they were injected with an amount of formulation corresponding to 10.8 mg/kg for both formulations. After injection, samples of plasma were collected from the rabbits at previously established sampling times of up to 175 days after injection. The results obtained are shown in FIG. 2.

Figure 2:
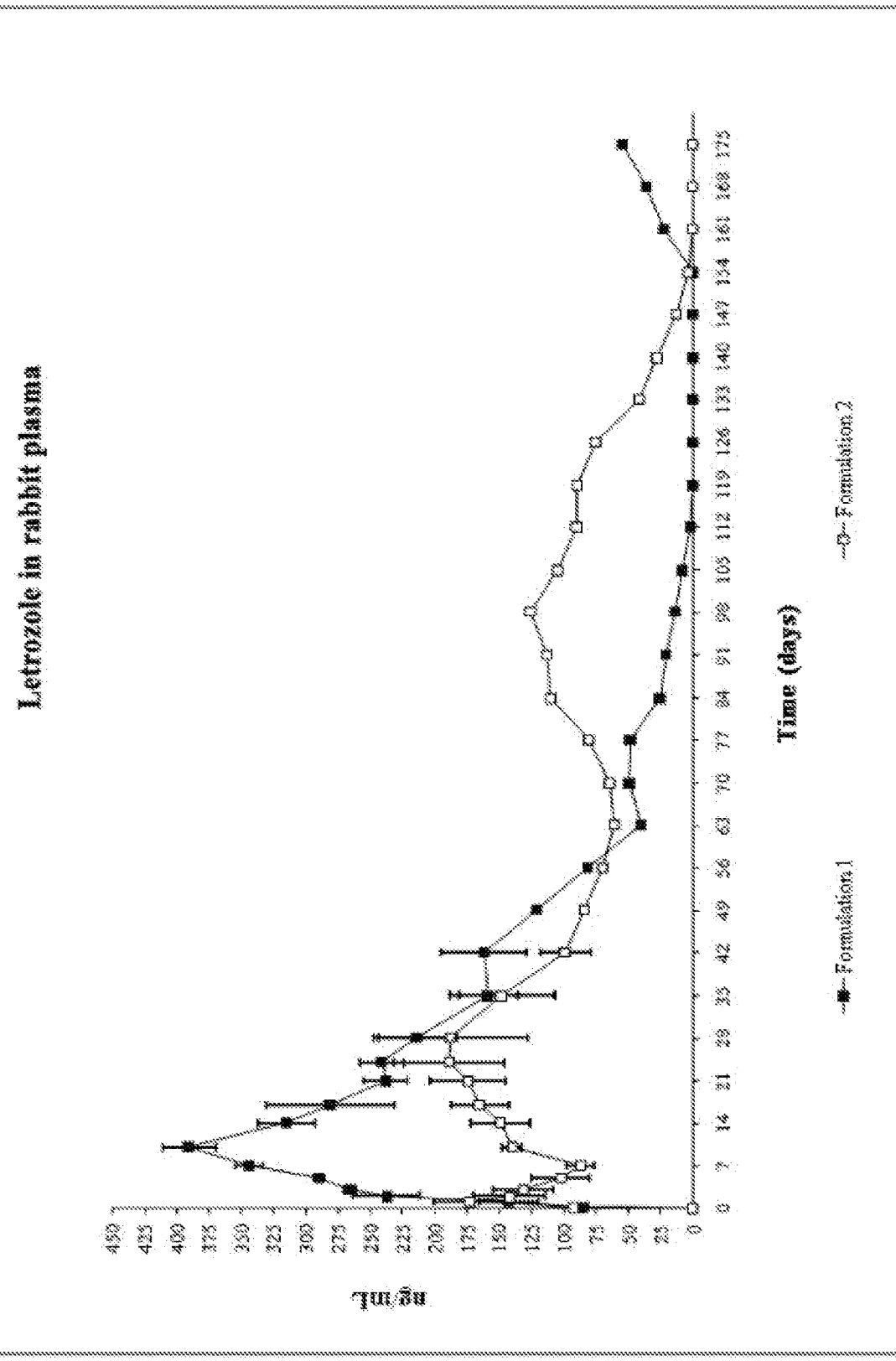
FIG. 2 depicts the plasma levels of letrozole (in ng/mL) obtained after the intramuscular administration to New Zealand white rabbits of the formulation described in example 2. The values shown correspond to the mean plasma levels obtained in three animals of each group.

FIG. 2 shows that administration of formulation 1 gave rise to very high initial letrozole plasma levels after injection. However, the levels progressively reduced until the levels were undetectable at 119 days. Formulation 2, on the other hand, resulted in significantly high levels over a clearly longer period of time. The high hydrophilicity of the polymer with the carboxylic terminal group and its higher wettability compared to the polymer with ester termination is probably behind the higher release of the active ingredient over the early phases of the study. Formulation 2, however, was able to modulate release of letrozole to a higher degree than formulation 1, giving rise to levels that were more sustainable overtime. The % area under the curve of letrozole plasma levels in each formulation over the total area under the curve are shown in the following table.

| Formulation | % AUC first 3 days | % AUC up to day 30 | AUC total (ng h/ml) |
|---|---|---|---|
| 1 | 3.981 | 66.630 | 328086.1 |
| 2 | 2.806 | 36.651 | 352267.6 |

Accordingly, in some embodiments, the PLA in the composition is an end-capped PLA (PLA-e).

Example 3: Study of the Influence of the Terminal Group of the Polymer in Beagle Doqs Evaluation of the influence of the terminal carboxylic or ester (N-capped) group of the polymer was evaluated by the use of the formulations described below:

Formulation 1: Formulation of Lactic Acid Polymer Terminating in a Carboxylic Group

| | Ingredient | Amount (mg, % wt) |
|---|---|---|
| Syringe 2.25 ml male | Lactic acid polymer (carboxylic terminal group) of intrinsic viscosity of 0.3 dl/g, irradiated as raw material at 10 kGy. | 107.6 (31.1%) |
| | Dimethyl sulfoxide | 151.7 (43.9%) |
| Syringe 2.25 ml female | Letrozole | 86.5 (25%) |

Weight ratio of DMSO to PLA is about 1.4:1. Weight ratio of polymer solution to letrozole is about 3:1. Weight ratio of PLA to letrozole is about 1.24:1. Weight ratio of DMSO to letrozole is about 1.75:1.

Formulation 2: Formulation with Lactic Acid
Polymer Terminating in an Ester Group

|  | Ingredient | Amount (mg) |
|---|---|---|
| Syringe 2.25 ml male | Lactic acid polymer (ester terminal group) of intrinsic viscosity of 0.3 dl/g, irradiated as raw material at 10 kGy. | 107.6 |
|  | Dimethyl sulfoxide | 151.7 |
| Syringe 2.25 ml female | Letrozole | 86.5 |

Letrozole particle sizes in formulations 1 and 2 were characterized by the technique of laser ray diffraction (Malvern Mastersizer 2000, suspended in water until obscuration of 9.41%) and had the following distribution (in % volume): d(0.1)=38.21 μm, d(0.5)=141.35 μm and d(0.9)=312.13 μm.

In both cases, reconstitution of the product was carried out by connection of the male and female syringes and successive movements of the plungers in both directions until complete solution of the polymer had been achieved.

The apparent viscosity at 25° C. of fully reconstituted formulation 2 gave a value of 2.865 Pa·s.

In parallel, the viscosity of the solution containing the components of the male syringe was evaluated, in amounts proportionally equivalent to those described (41.5% by weight of polymer with respect to the weight of solution) at 25° C. by the use of a rotational viscometer (Haake). The viscosity result values obtained are shown in the following table:

| Polymer (beta irradiated at 10 kGy as raw material) | Viscosity at 25° C. (Pa · s) |
|---|---|
| PLA-carboxylic terminal group | 1.221 |
| PLA-ester terminal group | 1.054 |

Study of In Vivo Release in Beagle Dogs

In the present example, formulations 1 and 2 were administered intramuscularly in the gluteus muscle of Beagle dogs with approximate body weight of 10 kg. Three animals were used for each group and they were injected with an amount of formulation corresponding to 86.5 mg/kg for both formulations. After injection, samples of plasma were collected from the dogs at previously established sampling times of up to 472 days after injection. The results obtained are shown in FIG. 3.

Figure 3:
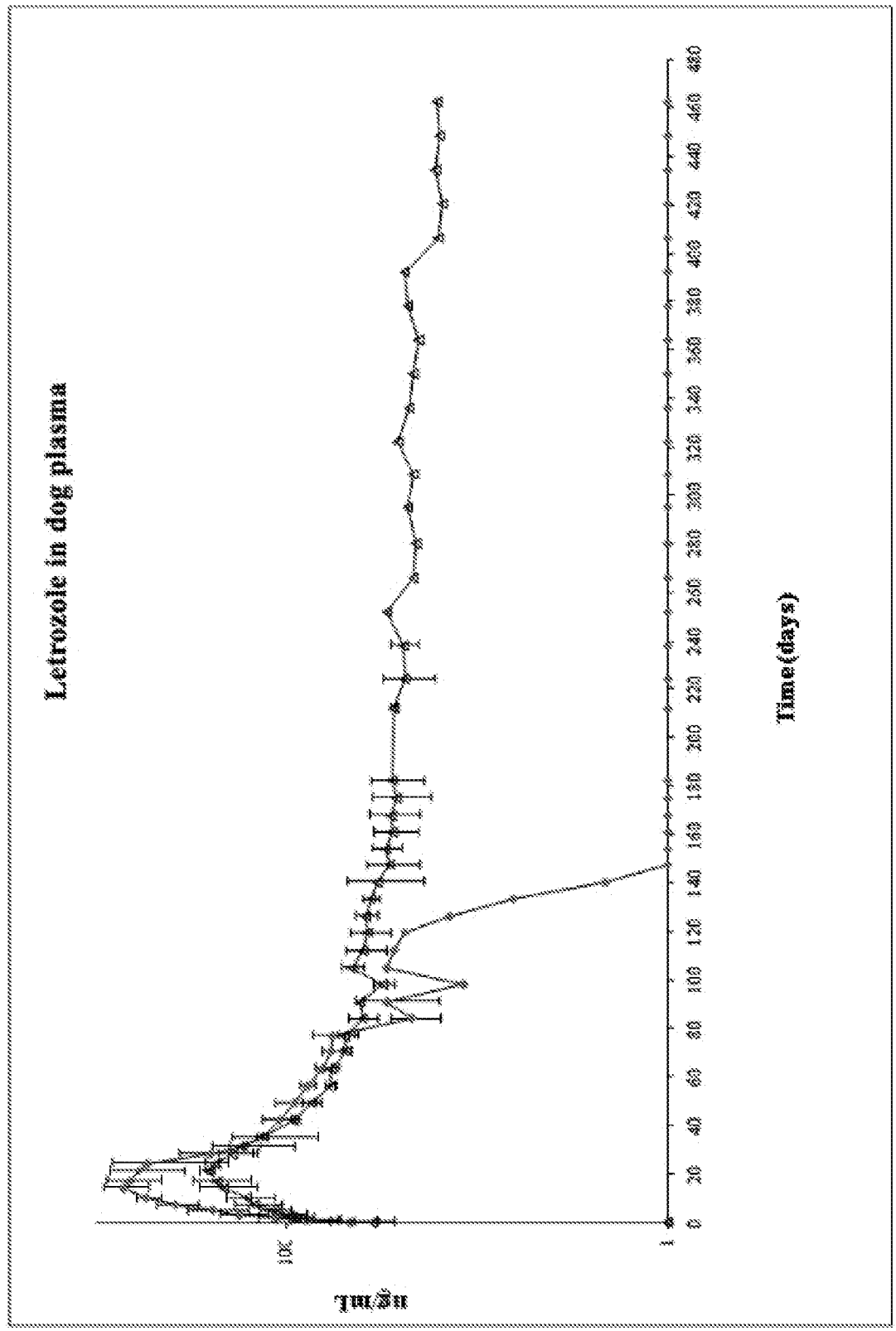
FIG. 3 depicts the plasma levels of letrozole (in ng/mL) obtained after intramuscular administration to beagle dogs the formulations described in example 3. The values shown correspond to the mean plasma levels obtained in three animals of each group.

FIG. 3 shows that the difference observed in the previous example between the two polymers was significantly higher in dogs. The lower body temperature of the Beagle dog (some 2.4° C. lower than the New Zealand white rabbit) slowed down the diffusion process, probably due to a combination of effects between the lower speed of hydrolysis of the polymers at the lower temperature and lower diffusion of the active ingredient across the matrix also due to the lower body temperature. A higher influence of polymer hydrophilicity in the kinetic profile of letrozole was observed in this situation of reduced diffusion and speed of degradation. The observation of a continuous increase in letrozole plasma levels over the first 14 to 21 days demonstrates an enterohepatic circulation phenomenon that has been demonstrated by population pharmacokinetic analysis of the data obtained (Nonmen). This enterohepatic circulation of letrozole is likely to be also observable in humans.

The % area under the curve of letrozole plasma levels in each formulation over the total area under the curve are shown in the following table:

| Formulation | % AUC first 3 days | % AUC up to day 30 | AUC total (ng h/ml) |
|---|---|---|---|
| 1 | 1.527 | 74.963 | 460177.6 |
| 2 | 0.537 | 36.940 | 482879.8 |

Example 4: Exploration of Compositional Range Limits

Formulations containing the ingredients and amounts specified below are prepared and evaluated according to any of Examples 1-3. The formulations provide a plasma profile such that the burst of the compound of general formula (1) (drug) is less than about 10% of the total AUC and not more than about 50% of the total AUC over the first 30 days after injection.

Formulation 4a: Formulation of Lactic Acid
Polymer Terminating in a Carboxylic Group

|  | Ingredient | Amount (% wt) |
|---|---|---|
| Syringe 0.5-5 ml male | Lactic acid polymer (PLA) | 15-42.5 |
|  | Dimethyl sulfoxide | 25-59.5 |
| (Same as above) Syringe 0.5-5 ml female | Letrozole or anastrozole | 15-50 |

Weight ratio of DMSO to PLA is about 1.0:1 to 2.3:1. Weight ratio of polymer solution to letrozole is about 1.0:1 to 5.7:1. Weight ratio of PLA to drug is about 0.4:1 to 2.8:1. Weight ratio of DMSO to drug is about 0.5:1 to 3.7:1.

Formulation 4b: Formulation of Lactic Acid
Polymer Terminating in a Carboxylic Group

|  | Ingredient | Amount (% wt) |
|---|---|---|
| Syringe 0.5-5 ml male | Lactic acid polymer (PLA) | 28-36 |
|  | Dimethyl sulfoxide | 38.5-52 |
| (Same as above) Syringe 0.5-5 ml female | Letrozole or anastrozole | 20-30 |

Weight ratio of DMSO to PLA is about 1.2:1 to 1.9:1. Weight ratio of polymer solution to drug is about 2.3:1 to 4.0:1. Weight ratio of PLA to drug is about 1.0:1 to 1.8:1. Weight ratio of DMSO to drug is about 1:1 to 3:1 or 1.5:1 to 2:1.

Formulation 4c: Formulation of Lactic Acid Polymer Terminating in a Carboxylic Group

|  | Ingredient | Amount (% wt) |
|---|---|---|
| Syringe 0.5-5 ml male | Lactic acid polymer (PLA) | 29.6-32.7 |
|  | Dimethyl sulfoxide | 42.2-45.6 |
| (Same as above) Syringe 0.5-5 ml female | Letrozole or anastrozole | 24-26 |

Weight ratio of DMSO to PLA is about 1.3:1 to 1.5:1. Weight ratio of polymer solution to drug is about 2.8:1 to 3.2:1. Weight ratio of PLA to drug is about 1.1:1 to 1.4:1. Weight ratio of DMSO to drug is about 1.7:1 to 1.8:1.

Formulation 4d: Formulation of Lactic Acid Polymer Terminating in an Ester Group

|  | Ingredient | Amount (% wt) |
|---|---|---|
| Syringe 0.5-5 ml male | Lactic acid polymer, ester terminal group (PLA-e) | 15-42.5 |
|  | Dimethyl sulfoxide | 25-59.5 |
| (Same as above) Syringe 0.5-5 ml female | Letrozole or anastrozole | 15-50 |

Weight ratio of DMSO to PLA is about 1.0:1 to 2.3:1. Weight ratio of polymer solution to drug is about 1.0:1 to 5.7:1. Weight ratio of PLA to drug is about 0.4:1 to 2.8:1. Weight ratio of DMSO to drug is about 0.5:1 to 3.7:1.

Formulation 4e: Formulation of Lactic Acid Polymer Terminating in an Ester Group

|  | Ingredient | Amount (% wt) |
|---|---|---|
| Syringe 0.5-5 ml male | Lactic acid polymer, ester terminal group (PLA-e) | 28-36 |
|  | Dimethyl sulfoxide | 38.5-52 |
| (Same as above) Syringe 0.5-5 ml female | Letrozole or anastrozole | 20-30 |

Weight ratio of DMSO to PLA is about 1.2:1 to 1.9:1. Weight ratio of polymer solution to drug is about 2.3:1 to 4.0:1. Weight ratio of PLA to drug is about 1.0:1 to 1.8:1. Weight ratio of DMSO to drug is about 1:1 to 3:1 or 1.5:1 to 2:1.

Formulation 4f: Formulation of Lactic Acid Polymer Terminating in an Ester Group

|  | Ingredient | Amount (% wt) |
|---|---|---|
| Syringe 0.5-5 ml male | Lactic acid polymer, ester terminal group (PLA-e) | 29.6-32.7 |
|  | Dimethyl sulfoxide | 42.2-45.6 |
| (Same as above) Syringe 0.5-5 ml female | Letrozole or anastrozole | 24-26 |

Weight ratio of DMSO to PLA is about 1.3:1 to 1.5:1. Weight ratio of polymer solution to drug is about 2.8:1 to 3.2:1. Weight ratio of PLA to drug is about 1.1:1 to 1.4:1. Weight ratio of DMSO to drug is about 1.7:1 to 1.8:1.

Example 5

Compositions containing the ingredients and amounts specified below are prepared and evaluated according to any of Examples 1-3. The compositions provide a plasma profile such that the burst of the compound of general formula (1) (drug) is less than about 10% of the total AUC and not more than about 50% of the total AUC over the first 30 days after injection. The compositions provide therapeutic plasma levels of aromatase-inhibitor for a period of at least 60 days after administration.

| Formulation | Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|---|
|  |  |  |  |  | Drug | Polymer | Solvent |  |
| A | Letrozole | 100:0 | 0.30 | DMSO | 25 | 85.2 | 127.8 | 1.20 |
| B | Letrozole | 100:0 | 0.30 | DMSO | 25 | 63.9 | 149.1 | 0.26 |

The implantable formulations were prepared by completely dissolving the polymer in the solvent and subsequently adding the drug in said polymeric solution.

The injection of an amount of formulation equivalent to 5.4 mg letrozole to New Zealand White rabbits resulted in controlled initial plasma levels (first 3 days) with a duration period of at least 56 days when polymers having an inherent viscosity of 0.38-0.43 dL/g were used.

As used herein, the term about is taken to mean ±10%, ±5% or ±1% of a specified value.

The invention claimed is:
1. An injectable composition consisting of
about 25% wt of drug, which is letrozole, wherein the drug has a particle size distribution selected from any of the following <10% of the particles are less than 20 microns, <10% of the particles are greater than 350 microns, and a d0.5 between 70-200 microns; or d0.1 of 38.21 microns, d0.5 of 141.35 microns, and d0.9 of 312.13 microns; and
the remaining balance of said injectable composition consisting of polymeric solution consisting of 57-60% wt of DMSO; and 40-43% wt of biodegradable poly (lactic acid) polymer (PLA), wherein
the polymeric solution has a viscosity in the range of 0.8-1.5 Pas, as measured at 25° C.; and
the drug is suspended in the polymeric solution.

2. The injectable composition of claim 1, wherein ≤20% wt of the drug is dissolved in the polymeric solution.

3. The injectable composition of claim 1, wherein the PLA has been irradiated with beta-radiation.

4. The injectable composition of claim 1, wherein the polymer has been lyophilized.

5. The injectable composition of claim 1, wherein the PLA is end-capped with a carboxylic acid group.

6. The injectable composition of claim 1, wherein the PLA is end-capped with an ester group.

7. The injectable composition of claim 1, wherein the maximum volume of the injectable depot composition is 2 mL containing a maximum of 500 mg of the drug.

8. The injectable composition of claim 1, wherein following administration to a subject, the AUC of the burst of drug is less than about 10% of the total AUC after administration and not more than about 50% of the total AUC over the first 30 days after administration.

9. The injectable composition of claim 1, wherein following administration to a subject, the plasma level of letrozole is sufficient to provide an in vivo suppression of serum estrogens estrone (E1) and estradiol (E2) of at least about 50% E2 and at least about 70% E1 in the steady state during a dosing period.

10. A kit suitable for the in situ preparation of the injectable composition of claim 1, wherein prior to preparation of the injectable composition, the kit comprises a) the drug and the polymer in solid form in a first container, and the DMSO is in a second container; b) the drug in a first container in solid form and the polymeric solution in a second container in solution; or c) the drug, the polymer, and the DMSO in a single container.

11. The kit of claim 10, wherein the PLA has been irradiated with beta-radiation.

12. A method of treating cancer that is therapeutically responsive to the aromatase inhibitor letrozole or a metabolite thereof comprising administering to a subject in need thereof a therapeutically effective amount of letrozole in the composition of claim 1.

13. The method of claim 12, wherein said composition is administered intramuscularly and following said administering, the AUC of the burst release of the drug is less than about 10% of the total AUC after administration and not more than about 50% of the total AUC over the first 30 days after administration.

14. The method of claim 12, wherein said composition is administered intramuscularly and following said administering, the plasma level of the drug is sufficient to provide an in vivo suppression of serum estrogens estrone (E1) and estradiol (E2) of at least about 50% E2 and at least about 70% E1 in the steady state during a dosing period.

15. An injectable composition consisting of
about 25% wt of drug, which is letrozole, wherein the drug has a particle size distribution selected from any of the following <10% of the particles are less than 20 microns, <10% of the particles are greater than 350 microns, and a d0.5 between 70-200 microns; or d0.1 of 38.21 microns, d0.5 of 141.35 microns, and d0.9 of 312.13 microns; and the remaining balance of said injectable composition consisting of polymeric solution consisting of 57-60% wt of DMSO; and 40-43% wt of biodegradable poly (lactic acid) polymer (PLA), wherein the polymeric solution has a viscosity in the range of 0.8-1.5 Pas, as measured at 25° C.;

the drug is suspended in the polymeric solution;

the PLA has been irradiated with beta-radiation; and the PLA is end-capped with an ester group.

16. The injectable composition of claim 15, wherein ≤20% wt of the drug is dissolved in the polymeric solution.

17. The injectable composition of claim 15, wherein the polymer has been lyophilized.

18. A kit suitable for the in situ preparation of the injectable composition of claim 15, wherein prior to preparation of the injectable composition, the kit comprises a) the drug and the polymer in solid form in a first container, and the DMSO is in a second container; b) the drug in a first container in solid form and the polymeric solution in a second container in solution; or c) the drug, the polymer, and the DMSO in a single container.

19. The kit of claim 18, wherein the PLA has been irradiated with beta-radiation.

20. A method of treating cancer that is therapeutically responsive to the aromatase inhibitor letrozole or a metabolite thereof comprising administering to a subject in need thereof a therapeutically effective amount of letrozole in the composition of claim 15.

21. The method of claim 20, wherein said composition is administered intramuscularly and following said administering, the AUC of the burst release of the drug is less than about 10% of the total AUC after administration and not more than about 50% of the total AUC over the first 30 days after administration.

22. The method of claim 20, wherein said composition is administered intramuscularly and following said administering, the plasma level of the drug is sufficient to provide an in vivo suppression of serum estrogens estrone (E1) and estradiol (E2) of at least about 50% E2 and at least about 70% E1 in the steady state during a dosing period.

* * * * *